US009198897B2

(12) United States Patent
Merello et al.

(10) Patent No.: US 9,198,897 B2
(45) Date of Patent: Dec. 1, 2015

(54) METHODS AND COMPOSITIONS FOR DECREASING SALIVA PRODUCTION (75) Inventors: Marcelo Merello, Capital Federal (AR); Neal M. Farber, Waban, MA (US); Eyal S. Ron, Lexington, MA (US)

(73) Assignee: NeuroHealing Pharmaceuticals, Inc., Newton, MA (US)

( * ) Notice: Subject to any disclaimer, the term of this patent is extended or adjusted under 35 U.S.C. 154(b) by 2241 days.

(21) Appl. No.: 11/795,210

(22) PCT Filed: Jan. 19, 2006

(86) PCT No.: PCT/US2006/002206
§ 371 (c)(1),
(2), (4) Date: Jul. 13, 2007

(87) PCT Pub. No.: WO2006/078998
PCT Pub. Date: Jul. 27, 2006

(65) Prior Publication Data
US 2008/0102102 A1 May 1, 2008

Related U.S. Application Data (60) Provisional application No. 60/645,147, filed on Jan. 19, 2005.

(51) Int. Cl.
*A61K 31/44* (2006.01)
*A61K 31/46* (2006.01)
*A61K 31/40* (2006.01)
*A61K 9/00* (2006.01)
*A61K 9/70* (2006.01)
*A61K 31/00* (2006.01)
*A61K 47/10* (2006.01)
*A61K 47/38* (2006.01)

(52) U.S. Cl.
CPC .............. *A61K 31/40* (2013.01); *A61K 9/0056* (2013.01); *A61K 9/7007* (2013.01); *A61K 31/00* (2013.01); *A61K 31/46* (2013.01); *A61K 47/10* (2013.01); *A61K 47/38* (2013.01)

(58) Field of Classification Search
CPC .............................. A61K 31/44; A61K 31/46
USPC ....................................................... 514/203
See application file for complete search history.

(56) References Cited

U.S. PATENT DOCUMENTS

| 4,671,953 | A |   | 6/1987 | Stanley et al. |   |
|---|---|---|---|---|---|
| 4,849,246 | A |   | 7/1989 | Schmidt |   |
| 4,863,737 | A |   | 9/1989 | Stanley et al. |   |
| 4,876,092 | A |   | 10/1989 | Mizobuchi et al. |   |
| 4,925,670 | A |   | 5/1990 | Schmidt |   |
| 4,946,684 | A |   | 8/1990 | Blank et al. |   |
| 5,298,256 | A |   | 3/1994 | Flockhart et al. |   |
| 5,510,122 | A | * | 4/1996 | Sreebny et al. | 424/537 |
| 5,648,093 | A |   | 7/1997 | Gole et al. |   |
| 5,700,478 | A |   | 12/1997 | Biegajski et al. |   |
| 5,711,961 | A |   | 1/1998 | Reiner et al. |   |
| 5,785,989 | A |   | 7/1998 | Stanley et al. |   |
| 5,800,832 | A | * | 9/1998 | Tapolsky et al. | 424/449 |
| 6,177,096 | B1 |   | 1/2001 | Zerbe et al. |   |
| 6,552,024 | B1 | * | 4/2003 | Chen et al. | 514/252.16 |
| 6,635,658 | B2 |   | 10/2003 | Madera et al. |   |
| 6,756,051 | B1 |   | 6/2004 | Chen et al. |   |
| 2003/0068376 | A1 |   | 4/2003 | Chen et al. |   |
| 2003/0118653 | A1 |   | 6/2003 | Chen et al. |   |
| 2004/0022743 | A1 |   | 2/2004 | Nevo |   |

FOREIGN PATENT DOCUMENTS

| EP | 0 200 508 | 12/1986 |
|---|---|---|
| EP | 0 381 194 | 8/1990 |
| WO | WO 98/20862 | 5/1998 |
| WO | WO 9940898 | * 8/1999 |
| WO | WO 01/08681 | 2/2001 |

OTHER PUBLICATIONS

Christine et al. (The American Journal of Medicine, vol. 117, Issue 6, Sep. 15, 2004, pp. 412-419). Abstract only.*
Dental Product Spotlight. Sal-tropine. JADA, vol. 132, Jul. 2001. pp. 1021-1022.*
J. Takeuchi et al. (Pharmacology, Biochemistry and Behavior 72 (2002) 117-123).*
Swerdlow et al. ("A Study of Some Parasympatholytic and parasympathomimetic drugs". Anesthesia & Analgesia. 38(3):229-235, May/Jun. 1959).*
Invoice for Sale by Hope Pharmaceuticals, Inc. of Sal-Tropine® brand atropine sulfate to Jewett Drug Company (Dec. 6, 1995).
Web Archive listing and of archived page from Feb. 6, 1997 advertising Sal-Tropine® brand atropine sulfate for use as a drooling control compound.
"Atropine—Atropine Sulfate," in *AHFS Drug Information* (McEvoy, G. K., ed.) (American Society of Health-System Pharmacists, Inc., Bethesda, 2001), pp. 1188-1191.
Hasty, M. F., "Atropine Sulfate—A Drying Agent for Sealant Application," *Journal of the Southeastern Society of Pediatric Dentistry*, 3(1): 20 (1997).
"Dental Product Spotlight, Anticholinergics, Sal-Tropine," *Journal of the American Dental Association*, 132: 1021 (Jul. 2001).
Sales Brochure, Sal-Tropine®, Hope Pharmaceuticals (2000).
Schoenwald, Ronald David, "A Drug Absorption Analysis for the Mydriatic, Tropicamide, Using Pharmacological Response Intensities," (Ph.D. Thesis, Jun. 1971), Title page-p. xxi.
USP XXII, NF XVII (meeting at Washington, DC, Mar. 22-24, 1985), (United States Pharmacopeial Convention, Inc., Rockville, 1990) p. 124.
USP XXII, NF XVII (meeting at Washington, DC, Mar. 22-24, 1985), (United States Pharmacopeial Convention, Inc., Rockville, 1990) pp. 1239-1240.
Klein, D., "Treatments for Drooling," *ALS Messenger*, 6(1): 8 (Amyotrophic Lateral Sclerosis Association, Greater Los Angeles Chapter, Mar. 1999).

(Continued)

*Primary Examiner* — Jeffrey S Lundgren
*Assistant Examiner* — Chris Simmons
(74) *Attorney, Agent, or Firm* — Leon R. Yankwich; David G. O'Brien; Yankwich & Associates, P.C.

(57) ABSTRACT

The invention provides methods and compositions comprising an anti-cholinergic agent for decreasing saliva production and treating sialorrhea.

33 Claims, 1 Drawing Sheet

(56) References Cited

OTHER PUBLICATIONS

"Tropicamide," *PDR Generics 1995*, First Edition (Medical Economics, Montvale, New Jersey, 1995), p. 2757.
Murrin, K. R., "A Study of Oral Atropine in Healthy Adult Subjects," *Brit. J. Anaesth.*, 45: 475-480 (1973).
"Atropine Sulfate, U.S.P.—Atropinae Sulfas (Atrop. Sulf.)", *Accepted Dental Remedies*, (American Dental Association, Chicago, 1938), pp. 72-73.
*A Complete Priced List Products of the Lilly Laboratories*, 48 (Eli Lilly and Co., Indianapolis, Jan. 1938), pp. 256-259.
"Scopace®" (drug information, Hope Pharmaceuticals, Inc., Scottsdale, Dec. 2002).
"Tropicamide," *Martindale—The Extra Pharmacopoeia*, 29th Edition, (Reynolds, ed.) (The Pharmaceutical Press, London, 1989), p. 544.
Dei et al., "Synthesis, Characterization and Pharmacological Profile of Tropicamide Enantiomers," *Life Sciences*, 58(23): 2147-2153 (1996).
Giovambattista, Z., "Nebulized Scopolamine in the Management of Oral Dribbling: Three Case Reports," *Journal of Pain and Symptom Management*, 17(4): 293-295 (1999).
Office Action, dated Jul. 16, 2008, issued in Australian patent application No. 2006206252.
Office Action, dated Jun. 11, 2009, issued in Canadian patent application No. 2,593,492.
"Antimuscarinics" In *Martindale: The Complete Drug Reference*, 33rd edition, (Sweetman, S., editor) (Pharmaceutical Press, London, 2002), pp. 459-475.
Antonello et al., *J. Psychiatry Neurosci.*, 24(3): 250 (1999).
Borsadia et al., *Drug Delivery Technology*, 3(3): 63-66(May 2003).
Calderon et al., *Int. Clin. Psychopharmacol.*, 15: 49-52 (2000).
Comley et al., Austr. N.Z.J. Psychiatry, 34(6): 1033-1034 (2000).
"Flavoring Agents" In *Chemicals Used in Food Processing*, publication 1274 (National Academy of Sciences—National Research Council, Food Protection Committee, Washington, D.C., 1965) 63-258.
Freudenreich et al., *J. Clin. Psychopharmacol.*, 24(1): 98-100 (2004).
Heine et al., *Dev. Med. Child Neurol.*, 38(11): 1030-1036 (1996).
Hyson et al., *Mov. Disord.*, 17(6): 1318-1320 (2002).
*Kirk-Othmer Encyclopedia of Chemical Technology*, vol. 5, pp. 857-884 (Wiley-Interscience, John Wiley & Sons, New York, 2005).
Marks et al., *Int. J. Lang. Commun. Disord.*, 36 (Suppl.): 288-291 (2001).
Meningaud et al., *Oral Surg., Oral Med., Oral. Pathol., Oral Radiol., Endod.*, 101: 48-57 (2006).
Mier et al., *Arch. Pediatr. Adolesc. Med.*, 154: 1214-1218 (2000).
Rengstorff et al., *Am. J. Optom. Physiol. Opt.*, 59(2): 162-177 (1982).
Sharma et al., *Ann. Pharmacother.*, 38(9): 1538 (2004).
Sherman et al., *Gen. Dent.*, 47: 56-60 (1999).
Supplementary European Search Report and Opinion for European patent application No. 06719165.0 (Oct. 14, 2009).
Bachrach et al., "Use of Glycopyrrolate and Other Anticholinergic Medications for Sialorrhea in Children with Cerebral Palsy," *Clin. Pediatr.*, 37: 485-490 (1998).
Blasco et al., "Glycopyrrolate Treatment of Chronic Drooling," *Arch. Pediatr. Adolesc. Med.*, 150: 932-935 (1996).
Neverlien et al., "Glycopyrrolate treatment of drooling in an adult male patient with cerebral palsy," *Clinical and Experimental Pharmacology and Physiology*, 27: 320-322 (2000).
Titcomb, L., "Mydriatic-cycloplegic drugs and corticosteroids," *The Pharmaceutical Journal*, 263(7074): 900-905 (1999).

Antonello et al., "Clozapine and sialorrhea: a new intervention for this bothersome and potentially dangerous side effect", J. Psychiatry Neurosci., 24(3): 250 (1999).
Barajas-Lopez et al., "5-Hydroxytryptamine and atropine inhibit nicotinic receptors in submucosal neurons", Eur.J. Pharmacol., 414:113-123 (2001).
Chou et al., "The Effectiveness of 0.5% Atropine in Controlling High Myopia in Children", J. Ocul. Pharmacol. Ther., 13(1): 61-67 (1997).
Lazareno et al., "Pharmacological Characterization of Guanine Nucleotide Exchange Reactions in Membranes from CHO Cells Stably Transfected with Human Muscarinic Receptors ml-m4", Life Sciences, 52: 449-456 (1993).
Lazareno et al., "Characterization of Muscarinic M4 Binding Sites in Rabbit Lung, Chicken Heart, and NG1O8-15 Cells", Mol. Pharmacol., 18: 805-815 (1990).
Lloret et al., A double-blind, placebo-controlled, randomized, crossover pilot study of the safety and efficacy of multiple doses of intraoral tropicamide films for the short-term relief of sialorrhea symptoms in Parkinson's disease patients, J. Neurol. Sci., 310: 248-250 (2011).
Parker et al., "Interactions of atropine with heterologously expressed and native α3 subunit-containing nicotinic acetylcholine receptors", British Journal of Pharmacology, 138(5): 801-810 (2003).
Pharmacology of Antimuscarinic Agents, Laszlo Gyermek,. CRC Press, LLC, p. 323, (Harvey Kane ed. (1998).
Saw et al., "Interventions to Retard Myopia Progression in Children: An Evidence-based Update", Ophthalmology, 109(3): 415-421 (2002).
Shih et al., "Effects of Different Concentrations of Atropine on Controlling Myopia in Myopic children", J. Ocul. Pharmacol. Ther., 15: 85-90 (1999).
Tessier et al., "Clozapine and sialorrhea: update", J. Psychiatry Neurosci., 26(3): 253 (2001).
Thomsen et al., "Ipratropium Bromide Spray as Treatment for Sialorrhea in Parkinson's Disease", Mov. Disord., 22: 2268-73 (2007).
Titcomb, L.C., "Mydriatic-cycloplegic drugs and corticosteroids", The Pharmaceutical Journal, 263 (7074): 900-905 (1999).
Walline, J.J.; Lindsley, K.; Vedula, S.S.; Cotter, S.A.; Mutti, D.O.; Twelker, JD. Interventions to slow progression of myopia in children (Review), Cochrane Database of Systematic Reviews. (12): CD004916, 2011.
Wess, J., "Molecular Biology of Muscarinic Acethylcholine Receptors", Crit. Rev. Neurobiol., 10: 69-99 (1996) (Abstract only).
Yen et al., "Comparison of the effect of atropine and cyclopentolate on myopia", Ann. Ophthalmol. 21: 180-187 (1989).
Zwart R. & Vijverberg, H.P., "Potentiation and Inhibition of Neuronal Nicotinic Receptors by Atropine: Competitive and Noncompetitive Effects", Mol. Pharmacol., 52: 886-895 (1997).
De Simone et al., "Atropine Drops for Drooling: A Randomized Controlled Trial", Palliative Medicine, 20: 665-671 (2006).
Iwabuchi et al., "Effects of Cholinergic and Adrenergic Agonists on the Secretion of Fluid and Protein by Submandibular Glands of the Guniea-pig and the Mouse", Comp. Biochem. Physiol., 107C(2): 185-193 (1994).
Levy et al., "Role of IL-13 in CD4 T Cell-Development IgE Production in Atopy", Int. Arch. Allergy Immunol., 112: 49-58 (1997).
Matsui et al., "Multiple Functional Defects in Peripheral Autonomic Organs in Mice Lacking Muscarninic AcetylCholine Receptor Gene for the M3 Subtype", PNAS, 97(17): 9579-9584 (2000).
Walline, J.J.; Lindsley, K.; Vedula, S.S.; Cotter, S.A.; Muth, D.O.; Twelker, JD. Interventions to slow progression of myopia in children (Review), Cochrane Database of Systematic Reviews. (12): CD004916, 2011.

* cited by examiner

METHODS AND COMPOSITIONS FOR DECREASING SALIVA PRODUCTION

CROSS-REFERENCE TO RELATED APPLICATIONS

The present application is a US national phase filing under 37 U.S.C. §371 of international application PCT/US2006/002206, filed Jan. 19, 2006, designating the US, which claims priority to U.S. Provisional Application No. 60/645,147, filed Jan. 19, 2005.

FIELD OF THE INVENTION

The present invention provides compositions and methods for decreasing production of saliva in individuals. In particular, the invention provides compositions useful for the treatment of sialorrhea.

BACKGROUND OF THE INVENTION

A variety of conditions and situations present the problem of undesirable amounts of saliva in the mouth of an individual. Classically, "sialorrhea" has been defined as "excess production of saliva, or increased retention of saliva in the mouth" or "saliva beyond the margin of the lip", i.e., drooling, although the term sialorrhea has sometimes more loosely been used to describe "excessive saliva secretion". Sialorrhea, i.e., drooling, is a well known, but often not discussed, condition that affects patients with various neurological diseases and such conditions as Parkinson's disease, Lewy body disease, cerebral palsy, amyotrophic lateral sclerosis (ALS, otherwise known as Lou Gehrig's disease), muscular dystrophy and multiple sclerosis, as well as oropharyngeal carcinomas. Sialorrhea also affects individuals with mental and developmental disabilities, those who have sustained various brain injuries, and individuals who have had a stroke. Sialorrhea may also occur as the result of neuromuscular dysfunction, sensory dysfunction, motor dysfunction, parkinsonism, pseudobulbar palsy, bulbar palsy, multiple system atrophy, corticobasal degeneration, motor neuron diseases, and neurodegenerative diseases. Several other situations predispose the development of sialorrhea due to the imperfect control of orofacial, head, and neck musculature, as is commonly found, e.g., in patients with cerebrovascular accidents, head injuries, severe dental malocclusion, and mental retardation. Adverse drug reactions involving tranquilizers, anticonvulsants, and anticholinesterases (e.g., clozapine and other drugs used to treat schizophrenia, and remoxipride) can also aggravate sialorrhea by causing hypersecretion of saliva. Sialorrhea affects over 3 million people annually. A recent review of the etiology and management of the problem of drooling appears in Meningaud et al., *Oral Surg. Oral Med. Oral Pathol. Oral Radiol. Endod.*, 101: 48-57 (2006).

Depending on its degree, drooling can result in social and medical disability, impaired speech, or serious feeding difficulties. Unable to manage their oral secretions, affected persons are at increased risk of aspiration pneumonia, skin maceration, and infection. Care may be compromised since the frequent suctioning and cleaning that are required to maintain proper hygiene can become very burdensome.

There are also a variety of situations in which it is desirable to temporarily inhibit or reduce saliva production in otherwise healthy individuals. For example, it is often useful or even necessary to maintain an adequately dry oral field to perform various dental, orthodontic, periodontal, and oral surgical procedures. For example, it is very important to maintain a dry oral field during many dental procedures, including cementation and bonding procedures, amalgam and composite restorations, the applications of sealants, and impressions during restoration of both anterior and posterior teeth. The increasing reliance of modern dentistry on adhesive materials has renewed the interest in means to maintain a dry field. Undesired saliva accumulation and drooling during such procedures has largely been addressed by employing one or more objects or mechanical devices that must be inserted into the mouth of a patient, e.g., suction devices, cotton rolls, and rubber dams. Such objects and devices can be cumbersome for both patient and the attending oral healthcare professional, interfere with the use of other tools employed in a procedure, invoke a gag response in the patient, and generally contribute to patient distress. The oral healthcare profession is continually seeking means and methods that will contribute to decreasing both a patient's experience as well as perception of distress associated with various dental and other oral healthcare procedures. Clearly, means and methods to produce an adequately dry oral field in a patient's mouth that also eliminate the necessity for using various mechanical objects as mentioned above would be highly desirable and would likely enhance patient acceptance of various dental, orthodontic, periodontal, and oral surgical procedures.

Saliva is produced by both the major and minor salivary glands. There are three pairs of major salivary glands: the parotid, submandibular, and sublingual glands. These glands produce from 1-1.5 liters of saliva daily in a circadian rhythm: in the resting state 70% of the saliva is from the submandibular glands, 25% is from the parotid glands, and 5% is from the sublingual glands. Minor salivary glands located on the palate, buccal mucosa, and tongue produce modest amounts of saliva. The secretory innervation of the salivary glands is primarily under the control of the parasympathetic nervous system. Stimulation of the parasympathetic system causes profuse secretion of saliva. The resting secretory rate may increase by 5 to 10-fold upon stimulation (olfactory, tactile, and gustatory).

Saliva is crucial for normal hygiene and serves important digestive, immunological, and protective functions. The goal in treating drooling is to reduce drooling but maintain a moist, healthy oral cavity. To eliminate drooling risks the significant complication of xerostomia (dry mouth). Over the last few years, efforts have been undertaken to develop treatments for sialorrhea that also address the dry mouth complication as well. Available therapies for treating sialorrhea include a variety of surgical procedures, radiation therapy, absorption devices, the use of certain drugs, and speech and behavioral therapy. No single therapy has been documented to resolve sialorrhea satisfactorily in all patients.

Surgical management of sialorrhea includes re-routing the parotid or submandibular ducts, excision of the submandibular glands, or transection of the nerves innervating the parotid gland or submandibular gland. Selection of the procedure seems to be largely a physician/patient preference issue that involves balancing the increased morbidity of the gland excision or duct relocation procedures against the threat of recurrence and the loss of taste associated with the nerve severing procedures.

Radiation therapy has been shown to produce glandular atrophy and decreases secretions; however, the dose required for atrophy may produce xerostomia, and the potential risk of secondary malignancy exists. In most cases, it seems inappropriate to substitute the dangers of radiation for the alleviation of drooling. Nevertheless, when drooling occurs in association with a terminal illness, use of radiotherapy may be warranted.

Recently, treatments for sialorrhea have included the use of commercial preparations of botulinum toxin A or B (e.g., Botox® botulinum toxin A preparation by Allergan, Inc.; Dysport® botulinum toxin A preparation by Ipsen Biopharm; Myobloc® botulinum toxin B preparation by Elan Pharmaceuticals) that can be injected directly, for example, into the parotid salivary glands. Several clinical studies have shown improvements. The toxin needs to be injected directly into the parotid and submandibular glands in a procedure that requires a skilled physician under imaging support to locate the glands to be treated in order to avoid puncturing a nerve or a major blood vessel. Studies claim that the effects last for a few months at best. Typically, saliva production is decreased by about 50-60% in about half the patients. While injections of botulinum toxin could be an option for a small portion of patients, the procedure is expensive, invasive, and not free of risk for serious complications.

Research into medicinal therapy has focused on the use of systemic anti-cholinergic drugs, such as atropine, scopolamine, and glycopyrrolate, which have been shown to reduce the production of saliva. These drugs do not prevent the release of acetylcholine but antagonize the effect of this neurotransmitter on the effector cells. This action results in drying of the mouth through reduction of salivary gland secretions. However, current therapeutic doses and the route of administration of these drugs usually result in unacceptable side effects such as constipation, urinary retention, blurred vision, and restlessness that greatly limit the potential for widespread use of such therapies. Glycopyrrolate is an anti-cholinergic drug approved to treat ulcers. It has been shown to be effective in the control of excessive sialorrhea in children with developmental disabilities, however approximately 20% of the treated individuals experienced substantial adverse systemic side effects requiring discontinuation of medication (see, e.g., Mier et al., *Arch. Pediatr. Adolesc. Med.*, 154: 1214-1218 (2000)). Others studies employing systemic administration of glycopyrrolate have reported behavioral changes.

The use of atropine sulfate tablets (e.g., Sal-Tropin® atropine sulfate tablets, Hope Pharmaceuticals) to treat sialorrhea has been reported by Sherman (Sherman C. R, *Gen. Dent.*, 47: 56-60 (1999)). Side effects include mild stimulation to the central nervous system at low doses, while larger doses can cause mental disturbances and depression. Death from atropine poisoning, though rare, is usually due to paralysis of the medullary centers. Other reports detail similar consequences when using atropine (see, e.g., Sharma et al., *Ann. Pharmacother.*, 38(9): 1538 (2004); Comley et al., *Austr. N. Z. J. Psychiatry*, 34(6): 1033-1034 (2000); Antonello et al. (*J. Psychiatry Neurosci.*, 24(3): 250 (1999)).

Other pharmacological treatments have been proposed to treat sialorrhea including the use of amitriptyline (a tricyclic antidepressant) and clonidine (an alpha-2-selective adrenergic agonist). However, due to the lack of efficacy and/or a high incidence of side effects, these drugs have not been approved for the treatment of sialorrhea.

One of the persistent problems in treating sialorrhea is the lack of local therapy. The above treatments were administered systemically and had many adverse reactions. For example, many sialorrhea patients are not deemed appropriate for systemic medications due to concomitant medical illness.

A pilot study with seven patients conducted by Hyson et al. (*Mov. Disord.*, 17(6): 1318-1320 (2002)) showed that sublingually administered atropine was effective in achieving a decrease in salivation in patients with Parkinson's disease. No effect was noted after 30 minutes, and results were first observed three hours after the initial treatment. A 32% decrease was observed in the volume of saliva.

Freudenreich reported a study of patients who used sublingual ipratropium (a bronchodilator) for clozapine-induced sialorrhea (Freudenreich, *J. Clin. Psychopharmacol.*, 24(1): 98-100 (2004)). Patients were initially administered two doses of 0.03% ipratropium sprayed sublingually at bedtime. Dosing was subsequently increased to 3 times daily. Of the nine patients who tried sublingual ipratropium, most had a partial yet clinically meaningful response. Typically, the effect of the spray wore off after a few hours (range 2-8 hours). Intranasal application has also been reported to be effective for clozapine-induced sialorrhea (Calderon et al., *Int. Clin. Psychopharmacol.*, 15: 49-52 (2000)).

Ipratropium is structurally related to atropine but differs in one significant distinguishing feature in that ipratropium is a charged quaternary amine whereas atropine is a neutral tertiary amine. Typical quaternary amine anti-cholinergic agents include ipratropium, glycopyrrolate, methylatropine, and homatropine methylbromide. Quaternary ammonium compounds are less lipid-soluble than tertiary amines, their gastrointestinal adsorption is poor, and they do not readily pass the blood-brain barrier or conjunctiva. The charge of quaternary ammonium compounds presents a barrier to crossing membranes. Tertiary amine anti-cholinergic agents include atropine, hyoscyamine, scopolamine, hyoscine, eucatropine, homatropine, benzhexol, apoatropine, tropicamide, and cyclopentolate. A useful description of various anti-cholinergic drugs ("antimuscarinics") can be found in *The Complete Drug References* 34*th edition*, (The Royal Pharmaceutical Society of Great Britain, London, 2004).

None of the above-mentioned investigators optimized the dose and the dosage-form of the various drugs in order to target decreased sialorrhea. All of the investigators used a selected drug in its current, commercially available form as intended for treating an unrelated indication. As a result, some treatments required multiple administrations over a long period (up to a few days) in order for an effect to be noticed. Moreover, in addition to a long delay in producing an outcome, the effect of the drugs persisted longer than needed. The use of these drugs also produce various adverse, systemic effects such as blurred vision, photophobia, fast heart rate (tachycardia), and anhidrosis producing heat intolerance or impaired temperature regulation. Hyson and Freudenreich stated that the unwanted side effects noted in their respective studies were related to swallowing the liquids and causing systemic effects or, e.g., inadvertent contact of ipratropium with the eyes.

Furthermore, the results in the above-mentioned studies were limited by the methodology of the assessment that relied on patient self-report as determined by retrospective chart review. Placebo-controlled trials with the use of instrumentation to measure salivary flow will be needed to establish efficacy.

The problem with current systemic anti-cholinergic agents is that they take a relatively long time to take effect (i.e., hours), nerves throughout the body are affected, and patients are exposed to chronic 24-hour doses. Currently there is no completely safe therapy to resolve sialorrhea satisfactorily in all patients without significant side effects.

Clearly the need remains for an effective, easily administered treatment for sialorrhea and other situations where it is desirable to control or temporarily decrease saliva production.

SUMMARY OF THE INVENTION

The present invention addresses the foregoing needs by providing methods and compositions for temporarily decreasing (reducing or inhibiting) saliva production in an individual. Compositions of the invention provide a well-defined local efficacy, rapid onset, and a useful predetermined duration of effect. Accordingly, the compositions of the invention may be used to treat sialorrhea and other drooling conditions, as well as to provide a desirably drier oral field in otherwise healthy individuals.

In one embodiment, the present invention provides compositions comprising one or more anti-cholinergic agents to decrease saliva production. When such compositions are applied intra-orally to an individual the compositions described herein release an effective, local amount of the anti-cholinergic agent to temporarily decrease saliva production from one or more salivary glands underlying the mucosal epithelium of the mouth.

Preferred anti-cholinergic agents useful in the methods and compositions described herein are tertiary and quaternary amine anti-cholinergic agents such as tropicamide, glycopyrrolate, cyclopentolate, atropine, hyoscyamine, scopolamine, hyoscine, eucatropine, homatropine, benzhexol, benztropine, apoatropine, propantheline, pirenzepine, ipratropium, methylatropine, homatropine methylbromide, biperiden, procyclidine, a salt thereof, and combinations thereof. More preferably, an anti-cholinergic agent useful in the methods and compositions described herein is tropicamide, cyclopentolate, or glycopyrrolate.

Tropicamide is an example of an anti-cholinergic agent that provides a relatively rapid onset of its pharmacological effect, e.g., within 15 to 20 minutes, and therefore is particularly preferred for compositions and methods of the invention in which a relatively rapid onset of inhibition or reduction of saliva production is desired.

Compositions comprising an anti-cholinergic agent as described herein may optionally further comprise one or more excipients to provide one or more additional desirable features to the compositions. Such excipients useful in the invention may include a pharmaceutically acceptable buffering agent, a plasticizing agent, a muco-adhesive agent, a stabilizing agent, a taste-masking agent, a flavoring agent, a breath freshening agent, a coloring agent, an antiseptic agent, an inert filler agent, a preserving agent, nonionic polymer, anionic polymer, softening agent, swelling agent, chelating agent, foaming agent, and combinations thereof.

Compositions described herein may be prepared in various dosage forms for intra-oral administration. Such useful dosage forms may include, without limitation, oral sprays, oral drop solutions, candy compositions, gums, films, buccal patches, lingual dosage forms, sublingual dosage forms, and fast-dissolving tablets. Candy compositions include lozenges, lollipops, pastilles, and troches. Particular dosage forms may be preferred for a particular patient or situation. For example, film compositions according to the invention may be prepared for easy and socially acceptable placement in the mouth of patients who suffer from sialorrhea or otherwise drool. Candy compositions, e.g., a lozenge or lollipop, not only deliver an anti-cholinergic agent to the mouth to decrease saliva production but also induce a patient to swallow saliva, a particularly desirable feature for patients who lack or have a diminished swallowing reflex.

Intra-orally administrable, dissolvable solid compositions described herein may be formulated to control or adjust a number of parameters in order to optimize a decrease in saliva production for a particular patient population or application. Such parameters include, without limitation, muco-adhesion property, dissolution rate, organoleptic properties (taste, feel, breath-enhancement, and the like), and dosage of the incorporated anti-cholinergic agent that is released from the composition in the mouth of an individual.

Compositions may also be formulated to control the duration of decreased saliva productions.

Preferably, the time period of a sustained decrease in saliva production provided by a single dosage form described herein is about 6 hours or less, more preferably 4 hours or less, and most preferably 2 hours or less.

In a preferred embodiment, compositions as described herein are administered intra-orally to treat a patient for sialorrhea or other drooling condition.

In yet another embodiment, the compositions described herein may be administered to an individual in conjunction with (e.g., prior to, simultaneously, or shortly after) another therapy. For example, compositions and methods of the invention may be used to produce an adequately dry oral field in an individual in preparation for or during various oral healthcare procedures, such as dental, orthodontic, periodontic, oral cosmetic, or oral surgical procedures. Compositions and methods described herein may also be used in patients prior to or during anesthesia in surgery or electroconvulsive therapy (ECT) in order to minimize secretions within the oral cavity and respiratory tract and, thereby, decrease the risk of aspiration or other complications due to saliva production. Compositions and methods described herein may also be used in combination with a variety of rehabilitation therapies such as speech therapy, biofeedback, positioning techniques, behavioral or oral motor therapy; physical therapy, occupational therapy, and/or sensory stimulation.

In still another embodiment, the compositions and methods described herein for treating sialorrhea may be combined with one or more other therapies for treating sialorrhea including, but not limited to, surgery, radiation, botulinum toxin injections, intra-oral prostheses, medical devices, and combinations thereof.

In other embodiments, the present invention provides treatments to decrease saliva production in animals, to control halitosis, and for motion sickness.

DETAILED DESCRIPTION OF THE INVENTION

The invention provides compositions and methods for reversibly decreasing (inhibiting or reducing) saliva production in the mouth of an individual (human or other mammal). Accordingly, the compositions and methods described herein may be used to inhibit or decrease undesirable saliva accumulation and drooling as may occur in sialorrhea or in any of a variety of situations where a relatively drier than normal oral field is desired, e.g., to conduct various dental or other medically useful procedures. Compositions and methods for decreasing saliva production as described herein have the advantages of being non-invasive, temporary, and easily controlled by an individual, attending healthcare professional, or healthcare provider.

In order that the invention may be more clearly understood, the following terms are defined below.

As noted above, classically, the term "sialorrhea" has referred to an "excess production of saliva, or increased retention of saliva in the mouth" or "saliva beyond the lip", which is usually presented as "drooling" by an individual. Accordingly, under this classical definition, a patient who suffers from sialorrhea is unable to properly swallow or expel saliva that accumulates in the mouth so that drooling occurs. Such inability to attend to saliva production may be owing to one or more impaired functions, such as, impaired swallowing reflex, poor head posture, abnormal structure of the oral cavity, or inadequate oropharyngeal motor function. Some sialorrhea patients have been found to actually produce lower than normal amounts of saliva. Thus, in the case of sialorrhea, whatever the actual level of saliva production is in a particular individual, the amount is clearly too great for the patient to control without drooling. As has been recognized previously in the field, a practical treatment approach is to diminish saliva production to some lower level that significantly diminishes drooling. Yet, current procedures (e.g., systemic administration of drugs, surgery, botulinum toxin injection, radiation therapy) for decreasing saliva production from salivary glands have a variety of untoward side effects, increase risks of permanent tissue damage (e.g., neural damage), and/or may be costly, and, thus, unattainable for many individuals. Moreover, even sialorrhea patients need some saliva for meals and adequate oral hygiene.

The terms "intra-oral" and "intra-orally" refer to a route of administration in the area of the mouth, specifically the mouth cavity and mucosal epithelium, without extending to the rest of the alimentary canal. The compositions described herein are specifically formulated for "intra-oral" administration. "Intra-oral" thus encompasses "buccal" wherein a composition is placed on the cheek tissue of the oral cavity, "lingual" wherein a composition is placed on the tongue, and "sub-lingual" wherein a composition is placed under the tongue.

The terms "oral" and "orally" are synonymous and refer to a route or mode of administration along the alimentary canal. Thus, tablets and capsules are typically administered "orally" such that they are placed in the mouth and swallowed in order to deliver their active ingredients to the gut for subsequent systemic absorption. Accordingly, the terms "oral" and "orally" are broader than and may, depending on context, encompass the terms "intra-oral" and "intra-orally".

The terms "parenteral" and "parenterally" refer to routes or modes of administration of a compound or composition to an individual other than along the alimentary canal. Examples of parenteral routes of administration include, without limitation, subcutaneous (s.c.), intravenous (i.v.), intramuscular (i.m.), intra-arterial (i.a.), intraperitoneal (i.p.), transdermal (absorption through the skin or dermal layer), nasal or pulmonary (e.g., by inhalation or nebulization for absorption through the respiratory mucosa or lungs), direct injections or infusions into body cavities or organs, as well as by implantation into the body or connection to the body of any of any a variety of drug delivery devices (e.g., implantation of a time-release composition, depot, or device that permits active or passive release of a compound or composition into the body).

An "oral field" refers to the area of the mouth of an individual to which a particular procedure or composition is to be directed for therapeutic, cosmetic, diagnostic, or prophylactic oral healthcare purposes. The term "oral field" may be used to refer to the entire mouth, e.g., in the case of treating drooling in an individual, or to a particular region to which a particular procedure or composition is directed for oral healthcare. Whether an oral field is "adequately" or "sufficiently" dry refers to the desired or preferred reduced level of saliva in the oral field as judged by a patient, e.g., to be relieved of drooling, or by an attending oral healthcare professional, e.g., in order to optimally treat a patient with a particular composition or procedure.

Unless specifically noted otherwise, it will be appreciated that descriptions of the use of compositions and methods of the invention to decrease saliva production or to produce an adequately dry oral field in a "dental" procedure or during use of anesthesia during surgery, will also be understood to encompass use in procedures that may be classified more precisely as orthodontic, periodontic, cosmetic, or surgical procedures.

By "pharmaceutically acceptable" is meant a material that is not biologically, chemically, or in any other way, incompatible with body chemistry and metabolism and does not adversely affect the desired, effective activity of an anti-cholinergic agent or any other ingredient of a composition described herein.

The meanings of other terms used to describe the invention are defined in the text below or have the meaning commonly understood by those skilled in the art, including oral healthcare, neurology, and pharmaceuticals fields.

The object of the invention is to temporarily (reversibly) decrease (inhibit or reduce) saliva production locally in the mouth of an individual. This goal is achieved by compositions described herein that comprise an active ingredient that is an anti-cholinergic agent (drug) prepared in a pharmaceutically acceptable, intra-orally administrable dosage form that provides an effective local amount of the anti-cholinergeric agent to the salivary glands while also minimizing systemic (circulatory) penetration of the drug.

The compositions and methods described herein may be used in any situation where it is desirable to decrease the amount of saliva produced by the salivary glands in the mouth of an individual (human or other mammals). Individuals who suffer from sialorrhea are unable to effectively swallow saliva as it is secreted into the mouth so that saliva accumulates until drooling occurs. Decreasing saliva production using the compositions and methods described herein is one strategy by which drooling can be avoided. Moreover, as the compositions and methods described herein decrease saliva production for a limited duration, the sialorrhea patient does not permanently lose the benefit of saliva production for eating, speaking, and general oral and dental health.

The invention is also useful in preparing otherwise healthy individuals for a dental and other oral healthcare procedure when the attending oral healthcare professional deems it desirable to minimize saliva production and accumulation. Compositions comprising an anti-cholinergic agent as described herein may be dissolved in the mouth of an individual to produce a temporary (reversible) decrease in saliva production to provide an adequately dry oral field for a period of time sufficient for the attending oral healthcare professional to treat the individual. Since the compositions dissolve away in the mouth, the invention should eliminate or greatly reduce the need for the attending professional to insert various objects, e.g., suction devices, cotton, and rubber dams, into the mouth of the individual as part of the procedure.

The compositions and methods described herein for decreasing saliva production may be administered to an individual in conjunction with (i.e., prior to, simultaneously, or shortly after) other therapies. Preferably, a composition described herein is used prior to or simultaneously with another therapy. For example, compositions and methods described herein may be used to avoid saliva production during anesthesia used in surgery or electroconvulsive therapy (ECT) to minimize secretions within the oral cavity and respiratory tract and thereby decrease the risk of aspiration or other complications due to saliva production and accumulation. Other therapies that may be used in combination with compositions and methods described herein include, but are not limited to, speech therapy, biofeedback, positioning techniques, behavioral therapy, oral motor therapy, physical therapy, occupational therapy, and/or sensory stimulation. The compositions of the invention may also be used in conjunction with other modes of treating sialorrhea including surgery, radiation, or botulinum toxin injections, intra-oral prostheses, medical devices, and combinations thereof.

Methods and compositions described herein may also be employed in conjunction with various procedures and treatments of veterinary medicine, e.g., anesthesia and dentistry, where it is desirable to decrease saliva production in an animal, and in controlling saliva production in otherwise healthy pets, e.g., certain breeds of dogs, where a condition analogous to sialorrhea in human may result in excess saliva production and dissemination that becomes a nuisance to pet owners.

Although the compositions described release a locally effective amount of an anti-cholinergic agent into the mouth cavity to decrease saliva production by underlying salivary glands, there may be additional benefits from such delivery systems. For example, compositions may be formulated to simultaneously provide treatments for motion sickness, halitosis, and hyperhidrosis.

Anti-Cholinergic Agents Useful in the Invention

A variety of anti-cholinergic agents (anti-cholinergic compounds) are known that may be employed in the compositions and methods of the invention. Such useful anti-cholinergic agents are tertiary or quaternary amines, including without limitation, tropicamide, glycopyrrolate, cyclopentolate, atropine, hyoscyamine, scopolamine, hyoscine, eucatropine, homatropine, benzhexol, benztropine, apoatropine, propantheline, pirenzepine, ipratropium, methylatropine, homatropine methylbromide, biperiden, procyclidine, and salts and combinations thereof.

Preferred anti-cholinergic agents useful in the compositions and methods described herein are the tertiary amines tropicamide and cyclopentolate, the quaternary amine glycopyrrolate, or combinations thereof.

An anti-cholinergic agent useful in the compositions and methods described herein may be neutral or a charged form of the agent, depending on the particular demands of the particular composition or method employed for treating an individual.

Use of tropicamide (also referred to as bistropamide, N-ethyl-N-(4-pyridylmethyl) tropamide) for the purpose of decreasing saliva production or in treating sialorrhea patients has not heretofore been described. Although some anti-cholinergic agents, such as, glycopyrrolate, atropine, scopolamine, and ipratropium, have been tested for the ability to treat sialorrhea, such agents were applied in their commercially available form designed for other applications (e.g., glycopyrrolate as tablets, scopolamine as a patch). As noted above, the results were never satisfactory for effective treatment of drooling as the particular anti-cholinergic drugs readily entered the circulatory system and persisted longer than needed, and individuals experienced a number of unacceptable adverse, systemic effects such as blurred vision, photophobia, fast heart rate (tachycardia), and anhidrosis producing heat intolerance or impaired temperature regulation. Tropicamide and cyclopentolate have been safely used for many years by ophthalmologists for diagnostic procedures and during ocular surgery. These agents block the effect of acetylcholine on the sphincter muscle of the iris and the accommodative muscle of the ciliary body. This results in dilation of the pupil (mydriasis) and paralysis of the muscles required to accommodate for close vision (cycloplegia). Mydriasis is required in order to provide for a more complete examination of the fundus, the vitreous and the periphery of the lens, and in various surgical procedures (e.g., vitrectomy, lens extraction, and intraocular lens implantation).

Tropicamide has an anti-cholinergic potency similar to atropine but has a substantially better safety profile. Tropicamide is an anti-muscarinic agent that blocks muscarinic receptors in the muscles of the eye that are involved in controlling the pupil size and the shape of the lens. By blocking these receptors, tropicamide produces dilatation of the pupil (mydriasis) and prevents the eye from accommodating for near vision (cycloplegia). For such use, tropicamide is formulated and sold for administration as eye drops to dilate the pupil and relax the lens so that eye examinations can be carried out thoroughly. The incidence of tropicamide systemic toxicity appears to be very low as no adverse reactions were reported in 10,000 patients receiving ophthalmic drops of tropicamide by one investigator and in 1000 patients by another (Rengstorff and Doughty, Am. J. Optom. Physiol. Opt., 59(2): 162-177 (1982)). Importantly, tropicamide has a more rapid onset and a shorter duration of effect than atropine. For example, in ophthalmic uses, tropicamide produces mydriasis within 15-20 minutes of instillation and recovery is in 3-8 hours, whereas the peak mydriasis effect by atropine is in the range of 30-40 minutes.

Like tropicamide, cyclopentolate is another rapid onset anti-cholinergic (anti-muscarinic) agent that is commonly used in ophthalmic procedures to dilate the pupil (mydriasis) and prevent the eye from accommodating for near vision (cycloplegia). Cyclopentolate formulated and sold for administration as eye drops to dilate the pupil and relax the lens so that eye examinations can be carried out thoroughly. It is also used to relax the muscles that inflame and over-contract in the eye in conditions such as uveitis. Irises that are dark in color require larger doses of eye drops as the pupils do not dilate as easily in response to the drug. The maximum effect occurs within 25 to 75 minutes and last for 8 hours although some effects may persist for up to several days.

The quaternary amine, glycopyrrolate (also referred to as glycopyrronium bromide or 3-($\alpha$-cyclopentylmandeloy (osy)-1,1-dimethylpyrrolidinium bromide), also has several properties that make it particularly suitable for use in the compositions and methods described herein. In particular, based on systemic administration data, glycopyrrolate has a relatively rapid onset and a duration of effect that is longer than that of tropicamide. Accordingly, compositions of the invention comprising glycopyrrolate are particularly useful in providing a somewhat longer period of inhibition or reduction of saliva production, e.g., approximately 6 hours or less. Moreover, glycopyrrolate only poorly penetrates the blood-brain barrier, thereby increasing confidence that the drug has particularly low risks with respect to toxic or other untoward side effects.

As noted above, tropicamide is an example of anti-cholinergic agents that provide a relatively rapid onset of anti-cholinergic activity, e.g., typically within 15-20 minutes.

Such anti-cholinergic agents are particularly preferred for use in the compositions and methods described herein to provide an individual with a relatively rapid onset of the desired pharmacological effect, i.e., decrease in saliva production.

Selection of a particular anti-cholinergic agent for use in a composition or method described herein also can affect the duration of the anti-cholinergic effect. For example, compositions of the invention comprising tropicamide or cyclopentolate may be used to temporarily inhibit or reduce saliva production for several hours. Thus, in some compositions, different anti-cholinergic agents may be combined to provide an extended affect of decreased saliva production. In addition to selection of a particular anti-cholinergic compound or combinations of compounds, as discussed below, various formulations, e.g., slow-release formulations, may also be employed to extend the duration of the effect of a particular anti-cholinergic agent or combination of agents. Preferably, compositions of the invention decrease saliva production in an individual for 6 or less hours, more preferably 4 or less hours, and even more preferably 2 or less hours.

Assessment of Drooling and Saliva Production

There are two general means to assess sialorrhea: a subjective measurement provided by having a patient indicate an effect on a visual analog scale (VAS) and an objective quantitative saliva measurement obtained by inserting a cotton wad in patient's mouth for 5 minutes, and then either weighing the tared cotton wad or centrifuging and measuring the volume of liquid released (objective). In addition to the VAS, various other drooling scales may also be employed including, but not limited to, the Drooling Rating Scale (see, e.g., Marks et al., *Int. J. Lang. Commun. Disord.*, 36 (Suppl.): 288-291 (2001)), the Drooling Severity and Frequency Scale (Heine et al., *Dev. Med. Child Neurol.*, 38(11): 1030-1036 (1996)), and the Likert-type scale ranging from 1-5, and item 6 of the Activities of Daily Living (ADL) section of the Unified Parkinson's Disease rating Scale (UPDRS).

Routes of Administration and Compositions Useful in the Invention

Although anti-cholinergic agents may be administered to an individual by any of a variety of parenteral or non-parenteral routes, the preferred route for administering compositions (dosage forms, delivery systems) as described herein is intra-oral administration so that such compositions can release a local effective amount of an anti-cholinergic agent (e.g., tropicamide, cyclopentolate, glycopyrrolate) into the oral cavity for absorption across the mucosal epithelium to the underlying salivary gland(s). In addition to an anti-cholinergic agent, compositions described herein may also contain one or more other ingredients ("excipients") that provide one or more desirable features to improve performance of the compositions (e.g., administration, handling, storage, efficacy, patient acceptance).

Thus, dosage forms useful in the invention preferably provide a local therapy (i.e., proximal to the salivary glands) with minimal systemic effects, rapid onset of effect, and a desirable residence time for local application of the anti-cholinergic agent to treat sialorrhea or to otherwise provide an adequately dry oral field, e.g., as may be desirable for carrying out dental or other oral healthcare procedures. Dosage forms useful in the invention may include, without limitation, films, candy compositions (e.g., lozenges, lollipops), gums, fast-dissolving tablets, lingual and sublingual tablets, oral drops (oral drop solution), oral spray, metered doses, inhaler type devices, packaged "cotton swab type" applicators for applying an oral solution, and the like. Preferably, the dosage forms are also as small or thin as possible to minimize stimulating salivation. The dosage forms preferably offer improved ease of use and compliance by geriatric and pediatric patients. Some dosage forms described herein also are particularly useful for treating sialorrhea and other patients in which swallowing may be difficult, such as those with motor neuron disabilities. Preferably, once a dosage form is placed in the mouth it provides a local-releasing system that will release an effective amount of an anti-cholinergic agent to provide a sustained, but reversible, local decrease in saliva production for a predetermined duration. Minimizing systemic delivery of the active agent(s) is a desired feature of the methods and compositions of the present invention.

Individuals seeking to reduce drooling have reported that control of the time of onset and control of the duration of the saliva-decreasing effect are very important factors in selecting a therapy. The invention described herein provides aspects of control that are highly favored by patients. The invention may be used on a regular schedule once, twice, three times or more per day (e.g., between and after meals to allow normal saliva production during eating times) or on an occasional "as needed" basis.

Various solid dosage forms, such as lingual and sublingual tablets, troches, lozenges, lozenges-on-a-stick ("lollipops"), chewing gums, and buccal patches, have been used to deliver drugs systemically via the oral mucosal tissue. For example, U.S. Pat. No. 5,711,961 (to Reiner et al.) discloses a chewing gum for the systemic delivery of pharmaceuticals. The chewing gum delivery dosage form is primarily directed for patients who may be more disposed to self-administer a drug in chewing gum form as opposed to other less familiar dosage forms. In addition, the Reiner patent also discloses the use of the gum formulation to extend the duration of drug delivery.

Transmucosal delivery of drugs may also be accomplished through the use of patches, which are attached using an adhesive to mucosal surfaces in the oral cavity. An example of an oral transmucosal delivery method using a buccal patch is disclosed in U.S. Pat. No. 5,298,256 (to Flockhart et al.). The buccal patch may be designed as a "closed" delivery system, i.e., the environmental conditions inside the patch are primarily controlled by the formulation. Employing a closed delivery system can facilitate drug delivery, such as allowing the use of enhancers or other permeability facilitators in the formulation, which might otherwise be impractical. In an "open" delivery system, such as lozenges or sublingual tablets, the drug delivery conditions are influenced by the conditions of the surrounding environment, such as rate of saliva secretion, pH of the saliva, or other conditions beyond the control of the formulation.

Solid dosage forms such as lozenges and tablets are commonly used for oral transmucosal delivery of pharmaceuticals. For example, nitroglycerin sublingual tablets have been on the market for many years. The sublingual tablets are designed to deliver small amounts of the potent nitroglycerin, which is almost immediately dissolved and absorbed. On the other hand, most lozenges or tablets are typically designed to dissolve in the mouth over a period of at least several minutes, which allows extended dissolution of the lozenge, absorption of the drug, and systemic distribution.

A lozenge-on-a-stick dosage form of transmucosal drug delivery is disclosed in U.S. Pat. No. 4,671,953 (to Stanley et al.). In addition to being non-invasive and providing a particularly easy method of delivery, the lozenge-on-a-stick dosage form allows a patient or caregiver to move the dose in and out of the mouth to titrate the dose. This practice is called dose-to-effect, in which a patient or caregiver controls the administration of the dose until the expected therapeutic effect is achieved. One such commercially sold drug formulation is ACTIQ® (oral transmucosal fentanyl citrate, manufactured by Cephalon, Inc., Frazer, Pa.; see, U.S. Pat. Nos. 4,671,953; 4,863,737; and 5,785,989).

Solid dosage units may be made in a number of ways. In a high volume manufacturing facility, solid dosage units can be made by direct compression, injection molding, freeze-drying, or other solid processing techniques. Compression is a commonly used manufacturing process in making solid dosage units. A typical formulation of solid dosage form useful in the invention may comprise one or more active ingredients (e.g., an anti-cholinergic agent), bulking agents, binders, flavors, lubricants, and other excipients (see, below).

Preferred solid, intra-orally administrable dosage forms useful in the invention include various "candy" compositions. Candy dosage forms (e.g., lozenges, troches, pastilles, lollipops, and the like) are particularly useful to facilitate administration of various therapeutic agents to children and other individuals who may present distress and other problems with other forms of drug delivery, e.g., needle injections. Candy dosage forms of the invention comprise an anti-cholinergic agent and may, optionally, be formulated to include one or more ingredients (excipients) to enhance performance (e.g., handling, storage, efficacy, acceptance by patient). Examples of such excipients include, without limitation, a pharmaceutically acceptable buffering agent, a plasticizing agent, a muco-adhesive agent, a stabilizing agent, a taste-masking agent (e.g., to mask the taste of the anti-cholinergic agent), a flavoring agent (flavoring), a sweetener (preferably an artificial sweetener), a breath freshening agent, a coloring agent, an antiseptic agent, an inert filler agent, a nonionic polymer, an anionic polymer, a softening agent, a swelling agent, a chelating agent, a foaming agent, a preserving agent, and combinations thereof. Taste-masking agents, flavorings, and sweeteners are particularly useful for enhancing and sustaining the process of sucking on or licking a candy composition. Sucking or licking candy compositions also induces swallowing. Accordingly, such inducement to swallow is particularly desirable in the case of sialorrhea patients as such patients often lack or have a diminished swallowing reflex that is normally relied on to control and clear saliva that accumulates in the mouth.

Persons skilled in the art will also appreciate that intra-orally administrable candy compositions comprising an anti-cholinergic agent of the invention may also be formulated to dissolve at various rates depending on the particular formulations. By adjusting the various components, a candy composition may be formulated to provide a relatively hard or soft candy composition.

For individuals who can chew, gum compositions comprising an anti-cholinergic agent may also be employed to provide an intra-oral administration of an effective amount the anti-cholinergic agent to the oral cavity to decrease saliva production from underlying salivary glands. Gum compositions can also be formulated to include taste-masking agents, flavorings, and breath enhancers (e.g., bubble gum and other flavors, see below) in order to prolong the use of the gum and the release of the anti-cholinergic agent into the oral cavity. As with candy compositions, chewing a gum composition may also induce swallowing which is particularly desirable in treating sialorrhea patients.

Another useful dosage form is a film composition (e.g., films, strips, disks) comprising an anti-cholinergic agent. Such compositions are formulated to provide a thin dry film that can be placed in the mouth where it dissolves upon contact with saliva or mucosal surface to release an effective amount of an anti-cholinergic agent for absorption across the mucosal epithelium to the underlying local salivary glands in order to decrease saliva production. Film compositions may also be formulated to comprise a muco-adhering agent so that the film may be placed at and adhere to a preferred location in the mouth, e.g., the cheek, and not subsequently float to another location. Consequently, such films are not readily swallowed, but will reside exclusively in the mouth to release the anti-cholinergic agent locally in the area of the salivary glands.

Various types of rapidly dissolving (quick-dissolving) intra-orally administrable film compositions have been described (see, e.g., Borsadia et al., *Drug Delivery Technology* 3(3): May 2003); U.S. Pat. Nos. 6,177,096; 5,700,478; 6,552,024; and 6,756,051; incorporated herein by reference), and these can be readily adapted to incorporate an anti-cholinergic agent for local intra-oral release as described herein.

Quick-dissolving oral mucosal delivery film devices have also been described in U.S. Patent Application Publication US 2003/0118653 A1 (publication date: Jun. 26, 2003) and US Patent Application Publication US 2003/0068376 A1 (publication date: Apr. 10, 2003) that may also be used to provide a means of intra-oral administration of an anti-cholinergic agent to decrease saliva production. Such dosage forms provide a mucosal surface-coat-forming film that will adhere to the mucosal epithelium and then release an effective amount of the incorporated anti-cholinergic agent.

A variety of film dosage forms have been described, one or more aspects of which may also be employed to prepare compositions comprising an anti-cholinergic agent as described herein. Some film dosage forms are freeze-dried (lyophilized) preparations; a process that typically is more expensive to carry out than the more common procedures for manufacturing to tablets (see, e.g., U.S. Pat. No. 5,648,093). Such freeze-dried preparations may also be brittle and fragile when handled and must be kept in dry conditions to avoid disintegration. However, the instability of freeze-dried preparations has been reduced somewhat by the addition of mannitol (see, e.g., U.S. Pat. No. 4,946,684). PCT publication No. WO 98/20862 describes a film that can be formed according to a method that does not utilize freeze drying and avoids problems described in the art such as rigidity of the films, delayed softening, and poor solubility in the mouth. U.S. Pat. No. 4,876,092 describes an improved sustained release preparation applicable to the oral cavity that can be adhered on the mucous membrane in the oral cavity for a long period of time and can gradually release a pharmaceutically active agent through the mucous membrane in the oral cavity, suitable for administering a medicament. European Publication Nos. EP 0 200 508 and EP 0 381 194 describe the use of polyethylene films, polyvinyl acetate, ethylene-vinyl acetate copolymers, metal foils, laminates of cloth or paper and a plastic film, and similar materials as soft film supports, whereby synthetic resins like polyethylene, vinyl acetate homopolymers, and ethylene-vinyl acetate are the preferred materials. U.S. Pat. Nos. 4,925,670 and 4,849,246 describe the use of swellable polymers such as gelatins or cornstarch as film forming agents, which upon application to the oral cavity slowly disintegrate, thereby releasing an active ingredient incorporated in the film. Further described is a film described in PCT publication No. WO 98/20862 for use in the oral cavity that can contain a cosmetic or pharmaceutical active substance, however, it relies on the use of at least two different non-ionic surfactants to achieve immediate wettability. An anti-cholinergic agent in a film composition of the invention may also be encapsulated within a second polymer having dissolution properties that are different from those of the film. More than one active agent may be included in the film. The dosage unit may further include any of the following features, e.g., a dry film thickness in the range of 0.025-5 millimeters (mm), more preferably, less than 2.5 mm; a disintegration time in a range from 1-7200 seconds, preferably 60-1800 seconds and more preferably 300-1800 seconds; and a dissolution time in a range from 10-7200 seconds, more preferably 60-3600 seconds. One aspect of longer disintegration and dissolution time permits release of the drug over a longer period of time and prevents rapid washout of the anti-cholinergic agent from the oral cavity.

The film delivery systems of the invention preferably dissolve and release an effective amount of an anti-cholinergic agent and other desired ingredients on a moist mucosal surface in the mouth cavity. The preferred location in the mouth for placing a composition described herein is the lower cheek ("buccal administration") in order to minimize the distance between the anti-cholinergic agent released from the film composition and the submandibular salivary glands. The release of the anti-cholinergic agent preferably occurs without mastication or the need for intake of water. With particular reference to the oral cavity, the anti-cholinergic agents preferably will remain in the oral cavity for absorption across the mucosal epithelium of the mouth to inhibit or reduce saliva production from one or more of the underlying local salivary glands.

Depending on the optimal release kinetics and desired residence time of the anti-cholinergic agent in the mouth, the disintegration time and the dissolution time can be controlled within a prescribed range by adjustment of the formulation and the thickness of the film. In some cases, it is desirable for release of the anti-cholinergic agent to occur after dissolution of the film. For these applications, the active agent may be encapsulated in a material with dissolution properties that are different from those of the film itself. The delivery system can be prepared with zero order kinetic release of the contents or with first order kinetic release of the contents (e.g., 50% of the drug can be release within the first few minutes and the remaining over a longer time period). Encapsulation of the active agent also may be utilized to achieve masking of taste for active agents that are bitter. In some cases, two or more different anti-cholinergic agents may be included in the film.

The disintegration rate (rate at which a composition falls apart) and the dissolution rate (rate of appearance of anti-cholinergic agent from a composition) are parameters of film compositions that are known to be a function of the relative amounts of hydrophobic excipients present in the composition. As the relative content of hydrophobic excipients rises compared to other ingredients, the slower the film composition will disintegrate and dissolve. Hydrophobic compounds that are particularly useful for controlling disintegration and dissolution rates of film compositions of the invention include, but are not limited to, propylene glycol, polyethylene oxide, and polypropylene oxide.

Film compositions may also be prepared to provide a relatively quick dissolving dosage form with a prolonged retention of the anti-cholinergic agent in the mouth following dissolution to extend the residence time of the anti-cholinergic agent. The active anti-cholinergic agent may itself be incorporated into the film composition in a prolonged acting form, e.g., via encapsulation for slow release, altered particle size, mucosal tissue affinity, such that after the film quickly dissolves, the anti-cholinergic has a prolonged effect on reducing drooling. In addition to an anti-cholinergic agent, film compositions of the invention may also comprise one or more other ingredients to improve the organoleptic properties (smell, taste, texture, feel) of the film composition when placed in the oral cavity. Preferably, a film composition is perceived to "melt" in the mouth and leave a smooth pleasant feel and taste following dissolution. A variety of pharmaceutically acceptable agents or compounds ("excipients") may be employed to provide such desirable features to improve performance of the film compositions of the invention. Examples of such excipients include, without limitation, a pharmaceutically acceptable buffering agent, a plasticizing agent, a muco-adhesive agent, a stabilizing agent, a taste-masking agent, a flavoring agent, a breath freshening agent, a coloring agent, an antiseptic agent, an inert filler agent, a preserving agent, nonionic polymer, anionic polymer, softening agent, swelling agent, chelating agent, foaming agent, and combinations thereof.

Plasticizing agents that may be used in the compositions described herein may include, without limitation, glycerin, sorbitol, propylene glycol, polyethylene glycol, triacetin, triethyl citrate, acetyl triethyl citrate and other citrate esters.

Stabilizing agents that may be used in the compositions described herein include, but are not limited to, anti-oxidants, chelating agents, and enzyme inhibitors as exemplified by ascorbic acid, vitamin E, butylated hydroxyanisole, butylated hydroxytoluene, propyl gallate, dilauryl thiodipropionate, thiodipropionic acid, gum guaiac, citric acid, edetic acid and its salts, and glutathione.

Film dosage forms of the invention may vary in size, e.g., from 1 to 5 $cm^2$ for lingual placement and from 0.25 to 3 $cm^2$ for placement on the cheek or gums. The size is designed to provide convenience and non-intrusive application, yet minimize the swallowing of the dosage form.

Particularly preferred dosage forms of the invention have an adhesive layer or property, such as a muco-adhesive layer or property, which upon wetting serves to adhere the composition to the epithelial surface of the mouth. An adherent layer may also be designed to preferentially release the anti-cholinergic agent to the oral cavity and minimize release of the drug systemically. Preferably, such adherent dosage forms do not stick to the fingers when dry to facilitate inserting digitally or with an applicator.

Preferably, the intra-orally administrable, compositions described herein comprise an anti-cholinergic agent, or pharmaceutically acceptable salt thereof, per one dose in an amount ranging from 0.01 to 200 milligrams, more preferably 0.01 milligrams to 50 milligrams, even more preferably 0.1 milligram-20 milligrams.

Natural and artificial flavoring agents (flavors, flavorings) that can be used in the compositions of the invention include those known to persons skilled in the art. The flavors will be selected based on their inability to increase the salivatory response and/or to mask the taste of the anti-cholinergic agent. Typical flavorings may be chosen from synthetic flavor oils, flavoring aromatics, oleo resins, and extracts derived from plants, leaves, flowers, and fruits. Representative flavor oils include, without limitation; spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa, and various citrus oils, such as lemon, orange, grape, lime, and grapefruit. Also useful are fruit essences including apple, pear, peach, strawberry, raspberry, cherry, plum, pineapple, apricot, and the like. Flavoring agents may also be used individually or in combination. Other flavoring agents that may be used in compositions of the invention include aldehydes and esters including cinnamyl acetate, cinnamaldehyde, citral, diethylacetal, dihydrocarvyl acetate, eugenyl formate, p-methylanisole, and the like. Further examples of aldehyde flavorings include, but are not limited to, acetaldehyde (apple); benzaldehyde (cherry, almond); cinnamic aldehyde (cinnamon); citral, e.g., alpha citral (lemon, lime); neral, i.e. beta citral (lemon, lime); decanal (orange, lemon); ethyl vanillin (vanilla, cream); heliotropine, e.g., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, e.g., trans-2 (berry fruits); tolyl aldehyde (cherry, almond); veratraldehyde (vanilla); 2,6-dimethyl-5-heptenal, e.g., melonal (melon); 2-6-dimethyloctanal (green fruit); and 2-dodecenal (citrus, mandarin); cherry; grape; and combinations thereof. Generally, any flavoring or food additive, such as those described in *Chemicals Used in Food Processing*, publication 1274 by the National Academy of Sciences, pages 63-258, may be used. The effect of flavors may be enhanced using flavor enhancers such as tartaric acid, citric acid, vanillin, higher alcohols (see, e.g., U.S. Patent Application Publication No. US2004/0022743 A1, published Feb. 5, 2004), and the like.

The amount of flavoring employed is normally a matter of preference and subject to such factors as flavor type, individual flavor, and strength desired. Thus, the amount may be varied in order to obtain the result desired in the final composition. Such variations are within the capabilities of those skilled in the art.

Breath freshening agents useful in the compositions of the invention include menthol and other flavors or fragrances commonly used for oral hygiene or oral cleansing and include various quaternary ammonium bases.

The compositions of this invention may also contain one or more coloring agents (colors, colorants). These colorants are known in art as "FD&C" dyes and lakes. The materials acceptable for the foregoing spectrum of use are preferably water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino)diphenyl-methylene]-[1-N-ethyl-N-p-sulfonium benzyl)-2,5-cyclo-hexadienimine]. A full recitation of all FD&C and D&C dyes and their corresponding chemical structures may be found in the *Kirk-Othmer Encyclopedia of Chemical Technology, Volume* 5, pages 857-884 (Wiley-Interscience, 2005), incorporated herein by reference.

Nonionic polymers suitable for use in the invention include, but are not limited to, cellulose derivatives such as carboxymethylcellulose, hydroxyethyl cellulose, methylcellulose, hydroxypropyl cellulose, and hydroxypropyl methylcellulose; polyvinylpyrrolidone (PVP); polyvinyl alcohol (PVA); polyethylene oxide; modified starch; gelatin; agar; guar gum; locust bean gum; bentonite; scheroglucan; and combinations thereof. Preferably, a nonionic polymer useful in the invention is polyvinylpyrrolidone, hydroxypropyl methylcellulose, hydroxypropyl cellulose, polyvinyl alcohol, gelatin, polyethylene oxide, or a combination thereof. Most preferably, a nonionic polymer useful in the invention is polyvinyl alcohol, gelatin, hydroxypropyl methylcellulose, or a combination thereof.

Anionic polymers useful in the invention include, but are not limited to, polyacrylic acid such as carbopol, polycarbophil, poly(methyl vinyl ether-co-methacrylic acid), poly(2-hydroxyethyl methacrylate), poly(methylmethacrylate), poly (isobutylcyanoacrylate), poly(isohexycyanoacrylate), and polydimethylaminoethyl methacrylate; acacia; alginate; carrageenan; guar gum derivative; karaya gum; pectin; tragacanth gum; xanthan gum; dextran; sodium carboxymethyl cellulose ("sodium CMC"); hyaluronic acid; and combinations thereof. Preferably, an anionic polymer useful in the invention is carbopol, polycarbophil, alginate, carrageenan, pectin, sodium CMC, or a combination thereof. Most preferably, an anionic polymer useful in the invention is carbopol, polycarbophil, alginate, carrageenan, sodium CMC, or a combination thereof.

Softening agents suitable for use in the invention include, but are not limited to, propylene glycol, water, polyethylene glycol, glycerin, triacetin, diacetylated monoglycerides, diethyl phthalate, triethyl citrate, and combinations thereof. More preferably, a softening agent useful in the compositions of the invention is propylene glycol, water, glycerin, polyethylene glycol, or a combination thereof. Most preferably, a softening agent suitable for use in the invention is water, propylene glycol, glycerin, or a combination thereof.

Swelling agents (swelling modifiers) that are suitable for use in the invention may include either or both swelling retarding agents (swelling retarders, retarders) and swelling promoting agents (swelling promoters, promoters). Swelling retarders include, without limitation, wax such as beeswax, carnauba wax, paraffin wax, castor wax, spermaceti, petrolite, and microcrystalline wax; polyoxyethylene glyceride fatty acid derivatives; hydrogenated oils and fats such as castor oil, theobroma oil, partially hydrogenated soybean oil, glyceryl laurates, glyceryl myristates, glyceryl palmitates, and glyceryl stearates; long chain fatty acids and alcohols such as laruic acid/alcohol, myristic acid/alcohol, palmitic acid/alcohol, stearic acid/alcohol, and oleic acid; ethylene glycol distearate; polyoxyethylene sorbitol beeswax derivatives; sorbitan esters such as sorbitan tristearate, sorbitan sesquioleate, and sorbitan monooleate; propylene glycol monostearate; lecithin; poloxamers; and combinations thereof. Preferably, a swelling retarder for use in the invention is a polyoxyethylene glyceride fatty acid derivative, sorbitan ester, lecithin, poloxamer, wax, hydrogenated vegetable oil, or a combination thereof. Most preferably, a retarder useful in the invention is a polyoxyethylene glyceride fatty acid derivative, sorbitan ester, poloxamer, or a combination thereof. Also, a swelling retarder or combination of retarders used in the invention is preferably lipophilic. Most preferably, a retarder or combination of retarders useful in the invention exhibits a hydrophilicity lipophilicity balance ("HLB") of 5 or less.

Swelling promoters that are suitable for use in the invention include, but are not limited to, inorganic electrolytes such as sodium carbonate, sodium bicarbonate, potassium carbonate, potassium bicarbonate, sodium phosphate, potassium phosphate, sodium chloride, magnesium chloride, ferric chloride, and aluminum sulfate; triethanolamine; aminomethyl propanol; tromethamine; tetrahydroxypropyl ethylenediamine; and combinations thereof. Preferably, a swelling promoter useful in the invention is sodium bicarbonate, potassium bicarbonate, sodium phosphate, potassium phosphate, triethanolamine, sodium chloride, or a combination thereof. Most preferably, a swelling promoter useful in the invention is sodium bicarbonate, potassium bicarbonate, triethanolamine, or a combination thereof.

Chelating agents suitable for use with the invention include, but are not limited to, ethylenediaminetetraacetic acid ("EDTA") and salts thereof such as disodium EDTA, tetrasodium EDTA, and calcium disodium EDTA; diethylenetriaminepentaacetic acid ("DTPA") and salts thereof; hydroxyethyl ethylenediaminetriacetic acid ("HEDTA") and salts thereof; nitrilotriacetic acid ("NTA"); and combinations thereof. Preferably, a chelating agent useful in the invention is EDTA, HEDTA, salts thereof, or a combination thereof. Most preferably, a chelating agent useful in the invention is EDTA or a salt thereof.

Any of a variety of buffering agents may be suitable for use in the invention including, without limitation, sodium carbonate, sodium bicarbonate, potassium carbonate, potassium bicarbonate, sodium phosphates, potassium phosphates, sodium biphthalate, potassium biphthalate, sodium borate, glycine, tris, triethanolamine, piperazine, acetic acid, citric acid, tartaric acid, phosphoric acid, and combinations thereof. Preferably, a buffering agent useful in the invention is sodium carbonate, potassium phosphate, citric acid, tartaric acid, or a combination thereof. Most preferably, a buffering agent useful in the invention is sodium carbonate, citric acid, or a combination thereof. It is understood that a buffering agent includes its various non-ionic and ionic species depending on the final pH of a particular composition.

Foaming agents suitable for use with the invention include, but are not limited to, polyoxyethylene sorbitan esters ("Tweens"), polyoxyethylene alkyl ethers ("Brijes"), triethanolamine oleate, and combinations thereof. Preferably, a foaming agent useful in the invention is a polyoxyethylene sorbitan ester, polyoxyethylene alkyl ether, or a combination thereof. Most preferably, a foaming agent useful in the invention is a polyoxyethylene sorbitan ester or combination of polyoxyethylene sorbitan esters. Preferably, the foaming agent or combination of foaming agents useful in the invention exhibits an HLB in excess of 12.

Preserving agents (preservatives) suitable for use in the invention include, but are not limited to, anti-microbial agents and non-organic compounds. Preferred preserving agents useful in the invention include sodium benzoate, parabens and derivatives, sorbic acid and salts thereof, propionic acids and salts thereof, sulfur dioxide, sulfites, acetic acid and acetates, nitrites, nitrates, and combinations thereof.

Various other excipients may be present in the compositions of the invention, such as anti-oxidants, preservatives, mold-releasing agents, binding and bulking agents. Pharmaceutically acceptable buffering agents (see, above) and other types of pH control may also be added in order to provide for maximum drug efficiency. It will be appreciated that drugs in the non-ionized form are more readily transported across the mucosal membrane. Therefore, the pH conditions can be adjusted to minimize the percentage of drug absorbed systemically, and maximize the local effectiveness of the drug intra-orally.

Various dosage-form configurations are also possible employing the present invention. For example, layers of drug may be interspersed between layers of a dissolvable composition. Since the present invention provides different dissolvable matrix materials, which can be formed into a solid dosage-form, virtually any desired type of mold could be used for the formation of the dosage-form. Dosage units can be manufactured using extrusion or casting techniques.

Various containers and packaging options may be used for the intra-orally administrable, anti-cholinergic agent-containing compositions described herein, including but not limited to blister packages, pouches, individual foil wrappers, and the like. A particularly desirable feature of such containers and packages is to have an easy-opening design, which is particularly of concern for elderly and disabled individuals, who may have restricted ability, diminished hand strength or hand coordination, and, thus, are likely to be limited in the ability to open commonly used and safety packaging designs. Accordingly, it is particularly desirable that container and packaging for the compositions described herein have easy to open qualities so that they do not present a hindrance to use, and especially when an individual must administer a composition to him or herself. Another desirable feature of containers and packaging is that they be discreet such that an individual is comfortable using the composition even during a social event, without others noticing that the individual is taking a medicament to control drooling.

In order to more fully illustrate the invention, the following non-limiting examples are provided.

EXAMPLES

Example 1

Pilot Clinical Study of Tropicamide Solution to Treat Sialorrhea in Parkinson's Disease Patients In an open fashion, a group of four Parkinson's Disease (PD) patients (FLENI Institute, Argentina) complaining of sialorrhea were asked to administer a single dose consisting of 20 drops of Mydril® (1% tropicamide solution, Alcon) for a total of 10 mg tropicamide. Each milliliter (mL) contains 1% tropicamide with benzalkonium chloride 0.01% as preservative, sodium chloride, disodium EDTA and buffered to pH 4.0-5.8. The aim was to assess personal impression by the patients of their sialorrhea symptoms, including, drooling, speech performance, and social interference, as well as the presence of side effects, such as blurred vision, confusion, somnolence, tachycardia, hypotension, or any other discomforting sensation. The patients were evaluated for 2 hours in an outpatient clinic while resting in comfortable armchairs. They rated themselves on a visual analog scale by marking a line representing the amount of disability incurred by their sialorrhea both before and after the treatment by responding to the question: "How would you grade the effect of the drops that you were administered on your sialorrhea?"

The patients were fluctuating PD patients evaluated in the ON state in the morning, having eaten no food for one hour before the test. All patients were being treated with L-dopa, and, except for the tropicamide solution in this study, none of them were administered anti-cholinergics. The patients were instructed to keep the tropicamide drops in the mouth without swallowing, and special care was taken to avoid sublingual placement of the drops to try to avoid systemic absorption. The patients were instructed to perform some chewing like movements in order to distribute the drug homogeneously. The patients were instructed to fill the visual-analogical scale 1 hour after drug intake. In addition, they were asked about the latency of the effect, if any, and if the effect persisted before leaving.

Results

All patients improved after the administration of the tropicamide drops. The average improvement was 48±33% (range 10%-90%). Latency to the effect was within 30±8 minutes post-administration (range 20-40 minutes). None of the patients developed side effects or complications. Treatment did not affect heart rate (cause tachycardia), confusion, or somnolence. No complaint of photosensitivity was made.

Example 2

Figure 1:
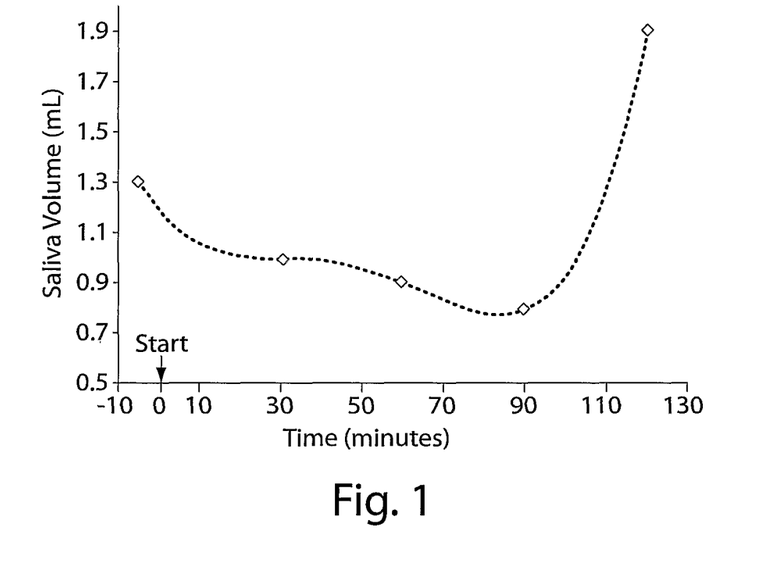
FIG. 1 shows a graph of saliva volume (milliliters) as a function of time (minutes) in an individual that was orally administered 20 drops of a 1% tropicamide solution as measured by the cotton plug method in Example 2. Dotted vertical line and arrow indicate time point of administration of tropicamide to the individual. See text for details.

Time Course of Saliva Production in Parkinson's Disease (PD) Patient Treated with Tropicamide Solution One PD patient was treated with 20 drops of 1% tropicamide as in Example 1. Sialorrhea was assessed in the patient over time by the quantitative cotton plug assay method. In the cotton plug method for measuring the volume of saliva, three cotton plugs were placed in the mouth, two at the level of each Stenon duct and one on the floor of the mouth, for 5 minutes and then removed using sterile pincers to measure the volume of saliva. The plugs were placed into 15 milliliter (ml) graduated Falcon tubes and centrifuged for 5 minutes at 3000 rpm, and the volume of the fluid (saliva) measured. The results of the cotton plug assay are shown in Table 1, below.

TABLE 1

| Sample | Time (min) | Volume (ml) | Variation (%) |
|---|---|---|---|
| 1 | −5.0 | 1.3 | 100 |
| 2 | 30.0 | 1.0 | 77 |
| 3 | 60.0 | 0.9 | 69 |
| 4 | 90.0 | 0.8 | 62 |
| 5 | 120.0 | 1.9 | 146 |

The results, shown in Table 1, above, and as plotted in FIG. 1, demonstrate that a significant effect occurred relatively fast, certainly within 30 minutes, and likely sooner. These data also support a duration of effect for up to 1.5 hours using the tropicamide solution.

Example 3

Long Term Treatment of Parkinson's Disease Patients with Tropicamide Solution

A group of Parkinson's Disease (PD) patients suffering from sialorrhea were instructed to use a 1% tropicamide solution on an out-patient basis to treat their excessive salivation. They were instructed to apply the drops to their tongues on an as needed basis. Two patients complained of the taste of the medication and discontinued use. Two patients reported that the treatment was useful and continued repeated use over a period of months.

Example 4

Fast-Dissolve Film Compositions

Fast-dissolve films are prepared as follows. Cellulose ether (21 g, Methocel E5), hydroxypropyl cellulose (17.5 g, Pullalan P-20) g, and polyethylene oxide (1.8 g, Polyox.RTM..WSR N-10) are mixed into 60 mL water containing 10 g of ethanol using a mechanical stirrer, and additional ingredients are added during the mixing as follows: 5 g tropicamide, 1 g peppermint, 0.5 g Aspartame, 0.8 g citric acid, 1 g polyoxyethylene hydrogenated castor oil (Cremophore RH-40), and 0.1 g benzoic acid. The temperature is maintained at room temperature. The solution is allowed to mix until uniform. It is then cast onto trays and allowed to dry. The resulting film is then cut into dosage forms ready for packaging.

Example 5

Preparation of Film Using Dry Extrusion Procedure

Polyethylene oxide (77.8 grams, Polyox.RTM.WSR N-10) is mixed using mechanical force and additional ingredients are added during the mixing as follows: tropicamide (5.5 g), peppermint (3.7 g), propylene glycol (3.7 g), Aspartame (3.0 g), citric acid (2.6 g), Cremophor EL 40 (3.7 g) and benzoic acid (0.05 g). The temperature is maintained at about 70° C. The blend is allowed to mix at 70° C. until uniform. It is then forced through an extrusion die to form a film 0.125 mm in thickness. The film is then cut into dosage forms ready for packaging.

Example 6

Slow-Dissolve Films Comprising Glycopyrrolate

Slow dissolving films comprising glycopyrrolate at doses of 2 and 4 milligrams (mg) are prepared as follows. A homogeneous mixture of ingredients is prepared in a coating solution basically as described in U.S. Pat. No. 6,756,051. Briefly, polyvinyl alcohol (36 g) and sodium alginate (20 g) are dissolved in water. Hydro-ethanolic solution of sorbitan monooleate (1 g) is then mixed into the polymer solution. The resulting solution is blended with glycopyrrolate (1 g), aspartame (0.82 g), benzoic acid (0.17 g), sodium EDTA (0.17 g), citric acid (1.4 g), red #40 (0.05 g), peppermint oil (1.7 g), polyoxyethylene hydrogenated castor oil (1.7 g), and propylene glycol (36 g). The solution is mixed and cast on a ribbon die to form a wet film. The film is dried and die-cut into suitable doses ready for packaging.

Example 7

Intra-Orally Dissolving Film Compositions Comprising Tropicamide

Intra-orally dissolving film compositions (also referred to as disks) comprising tropicamide at various doses (0.3, 1, and 3 mg, and placebo) were manufactured under contract by Lavipharm (Lavipharm Laboratories, Inc. East Windsor, N.J.) and using methods as basically described in U.S. Pat. No. 6,756,051. The thin flexible strips contain muco-adhesive properties that enabled them to be easily contoured to and be applied to buccal surfaces.

Example 8

Open Label Tests of Intra-Orally Dissolving Film Compositions Containing Tropicamide Several tests were conducted in human subjects to study the effect of tropicamide formulated in intra-oral dissolvable disks described in Example 7, above.

Study #1

This was an evaluation of the placebo and drug-containing disks conducted in a closed room while sitting and carrying on an otherwise normal conversation. Three subjects tested two tropicamide containing disks and one placebo disk. The subject who tested the placebo disk reported that the taste and texture were acceptable. The disks dissolved within several minutes. The subjects who tested the tropicamide-containing disks reported a sensation of drying of the mouth over a period of approximate 30 minutes.

Study #2

This was a single subject test of a 1 mg tropicamide disk in a comfortable room. No food or drink intake for approximately 2 hours before test. One disk was inserted in the mouth between gum and cheek on the lower right quadrant of mouth. The initial taste of the disk was acceptable, but a slightly artificial taste of the flavoring was noticed. The film dissolved in approximately 20 minutes and some local numbness was first noticed after 20 minutes. A sensation of dryness on the mouth was noticed after about 30 minutes. There was no obvious change in pupil size.

Study #3

Three subjects tested films containing 1 mg tropicamide. All sat in a comfortable room and had not eaten for at least one hour before.

Subject #1 used two (2) disks placed in the upper right side of the gum, between gum and cheeks. Observations noted by subject #1 included the following: dryness in the mouth was first observed 5 minutes after the films administration, peaked at 30 minutes, and lasted for 120 minutes. Films were dissolved in approx. 70 minutes.

Subject ∩2 used one (1) disk placed on the lower left below the teeth line. Observations noted by subject ∩2 included the following: dryness in the mouth was first observed 3 minutes after the film's administration, peaked at 45 minutes, started to decline at 60 minutes, and lasted for 90 minutes.

Subject ∩3 placed two (2) disks, one on each side of the lower jaw in the mouth. Observations noted by subject ∩3 included the following: dryness in the mouth was first observed 7 minutes after the films' administration, peaked at 15-30 minutes, and lasted for 90 minutes. Films were dissolved in approx. 50 minutes.

Study #4

Films (1 mg tropicamide) were tested in five PD patients in the FLENI Hospital, Argentina. The investigator reported that the films were clinically effective to reduce sialorrhea with a latency time of less than 10 minutes and duration of approximately one hour. No side effects were observed.

Example 9

Double Blind Crossover Study of Fast Dissolving Film Compositions Comprising Tropicamide Using Normal Human Volunteers This study was carried out by means of salivary monitoring using a visual analogue scale (VAS) in healthy volunteers and with intra-oral mucoadhesive films containing three dosages (0.3, 1, and 3 mg) of tropicamide and matching placebo as described in Example 7. The time of first noticeable dryness in the mouth and the time to complete disintegration of the film were noted. Comments about adverse events, taste, and tolerance were also recorded by the participants.

Tropicamide containing compositions were compared to baseline. The thin flexible strips contain a muco-adhesive property that enables them to be easily contoured to and be applied to buccal surfaces. They remain in the buccal cavity, releasing the drug over a defined period of time. They are fully dissolvable so that there is no residual material to throw away. The aim is to reduce salivary flow to create a drier mouth without producing high systemic blood levels of tropicamide, so avoiding the anti-cholinergic side effects associated with conventional oral formulations of this class of drug.

The principal aim of this study was to determine the salivary drying and duration of tropicamide from a slow-dissolve thin film strip (containing 0.03, 1, and 3 mg tropicamide) in healthy volunteers and to compare to placebo under similar conditions. The secondary aims of this study were to determine: time of first noticeable dryness in the mouth, time to complete disintegration of the film, and the acceptability and tolerance of the bioadhesive buccal films by the subject.

Study Scheme:

A blinded randomized crossover study in healthy volunteers. Each subject received and tested 4 coded/blinded doses of film products in a random order, with a wash out period of at least 24 hours between each administration.

The four doses administered were the 0.3, 1.0 and 3.0 mg containing tropicamide muco-adhesive thin films and a placebo film (no tropicamide). In each treatment, the product was blind labeled.

A visual analog scale assay was used with determinations every 15 minutes after applying the film to the cheek.

A thin film was removed from an individually wrapped pouch and placed in the inner cheek opposite the molars nearest to the submandibular gland. It was positioned with the fingers and the mucoadhesive property facilitated its adhesion.

Dissolve period: the dissolve period of the film was noted. It was defined as the time after which the film was no longer felt in the oral cavity. In no cases did the film detach from the buccal surface.

The volunteer recorded the tolerance to the buccal mucosa and overall feel during testing.

Results

Dryness. The VAS results obtained over time, i.e., at −10 (prior to administration), 15, 30, 45, 60, 75, and 90 minutes after buccal administration of the film, are shown in Table 2, below, and in FIG. 2.

TABLE 2

Figure 2:
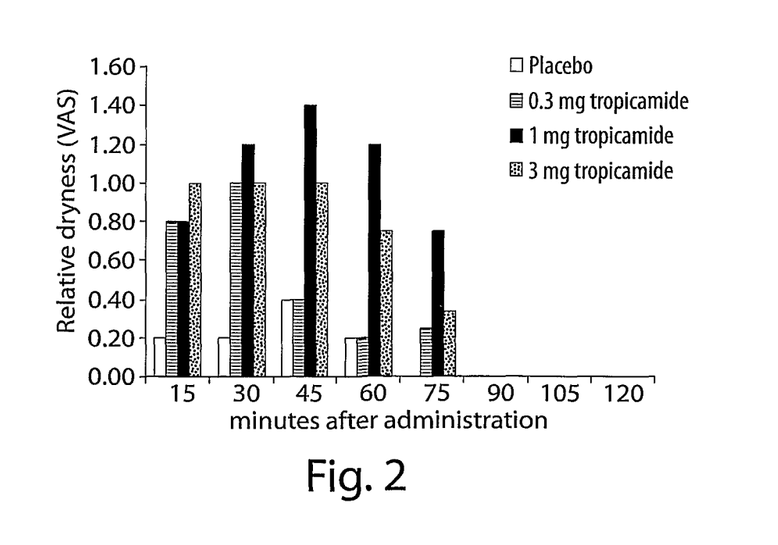
FIG. 2 shows bar graphs of the results of a double-blind trial of film compositions comprising 0 mg (Placebo, white bars), 0.3 mg (horizontally hatched bars), 1 mg (black bars), and 3 mg (stippled bars) of tropicamide to inhibit saliva production healthy adult volunteers as described in Example 9. Bars show the average (n=4) relative dryness as assessed on a visual analog scale (VAS) by four adult volunteers at −10 minutes (prior to administration), and 15, 30, 45, 60, and 75 minutes after administration of a film composition.

| Dose   | 15 min | 30 min | 45 min | 60 min | 75 min | 90 min |
|--------|--------|--------|--------|--------|--------|--------|
| Pbo    | 0.20   | 0.20   | 0.40   | 0.20   | 0.00   | 0.00   |
| 0.3 mg | 0.80   | 1.00   | 0.40   | 0.20   | 0.25   | 0.00   |
| 1 mg   | 0.80   | 1.20   | 1.40   | 1.20   | 0.75   | 0.00   |
| 3 mg   | 1.00   | 1.00   | 1.00   | 0.75   | 0.33   | 0.00   |

Pbo = placebo

First effect: In the group that noticed an effect, the first noticeable effect was between 10 and 15 minutes after applying the film to the cheek of the oral cavity.

Tolerance: For each product and for each administration by the volunteer the tolerance was recorded and found to be acceptable. There were no comments noting any unacceptable taste or smell.

Example 10

Protocol for a Clinical Trial (Pilot Study) of Intra-Orally Administrable, Fast-Dissolving Film Compositions Containing Tropicamide for Treatment of Sialorrhea A pilot study is performed of the bioavailability of single doses of tropicamide in intra-oral films versus ocular administration and of the clinical efficacy of two single doses of tropicamide in intra-oral films versus placebo for the short-term relief of sialorrhea symptoms in Parkinson's Disease (PD) patients (subjects). The duration of study for each subject is approximately 2 months.

The primary objective of the study is to evaluate the pharmacokinetics and bioavailability of intra-oral films containing 3 mg of tropicamide and ocular administration of the same dose in PD patients. The secondary objective of the study is to evaluate the safety and clinical efficacy of single doses of intra-oral films containing tropicamide (1 mg and 3 mg) to improve the short-term symptoms of sialorrhea in PD patients.

The study design is a prospective, randomized, crossover, two-phase, of two single dose treatments, in two forms of administration, in approximately 36 PD patients. Phase A (ocular administration of tropicamide) is not blinded for the patient and medical staff but is blinded for the clinical laboratory staff. Phase B (intra-oral administration of tropicamide 1 mg, 3 mg, or placebo) is blinded for medical staff, patients, and clinical laboratory staff. Patients are enrolled in the study in an outpatient, day clinic setting.

In Phase A, during visit #1, ocular tropicamide (3 mg) is administered to patients by an ophthalmologist, and patients are monitored for a period of at least 4 hours. There is then a 10-day washout period. In Phase B, for visits #2, #3 and #4, patients are randomized and assigned a specific sequence of visits. In between each visit there is a wash out period of 10 days. In each visit there is a saliva assessment. There is a 14-day safety follow up period.

In Phase A, the subjects in the study fast overnight, prior to admission to an outpatient clinic. Subjects are administered 1.5 mg tropicamide in each eye and are monitored by an ophthalmologist for a period of at least 4 hours, which is extended if required. Subjects have an intravenous cannula in a forearm vein. Blood sampling is conducted at the following times: 0 (pre-dosing), 5, 15, 30, 60, 90, 120, 180, and 240 minutes after the tropicamide administration. The blood samples (5 mL each) are centrifuged and kept frozen at −20° C.

In Phase B, the subjects are randomized into three groups. All groups receive intra-oral films containing placebo or tropicamide (1 mg or 3 mg), one film per visit. The sequence in which patients receive the 3 films is different for each group. In the first of the three visits of Phase B, blood samples are obtained according to the same scheduled described above for Phase A. During all 3 visits there are two efficacy assessments:

1. Visual Analog Scale (VAS) obtained at approximately 0 (pre-dosing), 15, 30, 45, 60, 90, 120 and 240 minutes after the drug (or placebo) administration.

2. Objective saliva assessment. The volume of saliva is measured according to the standard cotton plug method, 30 minutes before and 30, 60, 120 and 240 minutes after the drug (or placebo) administration.

Standard safety measures are used to ascertain tolerability and clinical response, including:

1. At screening: clinical evaluation, clinical laboratory analysis, ECG

2. During Phase A and Phase B: clinical evaluation, and ECGs. Special attention is taken to look for known adverse events seen after systemic administration of anti-cholinergics, such as confusion and related central nervous system phenomena, pupil dilatation, anxiety, fever, irritability, and ataxia.

All adverse events are recorded and followed up.

The primary efficacy assessment is the change in the VAS over the pre-dosing score, for each dose. The secondary efficacy assessment is the change in the volume of saliva over the pre-dosing measurement, for each dose.

All patents, applications, and publications cited in the above text are incorporated herein by reference.

Other variations and embodiments of the invention described herein will now be apparent to those of skill in the art without departing from the disclosure of the invention or the coverage of the claims to follow.

The invention claimed is:

1. A method for decreasing saliva production in an individual in need thereof comprising intra-orally administering to said individual an effective amount of a composition, the composition comprising as an active ingredient tropicamide and, optionally, an excipient, whereby saliva production in said individual is decreased.

2. The method according to claim 1, wherein said excipient, when present, is selected from the group consisting of a pharmaceutically acceptable buffering agent, a plasticizing agent, a muco-adhesive agent, a stabilizing agent, a taste-masking agent, a flavoring agent, a breath freshening agent, a coloring agent, an antiseptic agent, an inert filler agent, a preserving agent, nonionic polymer, anionic polymer, softening agent, swelling agent, chelating agent, foaming agent, and combinations thereof.

3. The method according to claim 2, wherein said excipient, when present, is a muco-adhesive agent.

4. The method according to claim 1, wherein said composition is in a dosage form selected from the group consisting of an oral spray, oral drop solution, film, candy composition, gum, buccal patch, lingual tablet, sublingual tablet, and fast-dissolving tablet.

5. The method according to claim 4, wherein said dosage form is selected from the group consisting of a candy composition, a film, and a gum.

6. The method according to claim 5, wherein said dosage form is a film.

7. The method according to claim 5, wherein said dosage form is a candy composition.

8. The method according to claim 7, wherein said candy composition is a lozenge or a lollipop.

9. A method for treating sialorrhea or drooling in an individual in need thereof comprising intra-orally administering to an individual in need of such treatment an effective amount of a composition, the composition comprising as an active ingredient tropicamide and, optionally, an excipient, whereby saliva production in said individual is decreased.

10. The method according to claim 9, wherein said composition consists essentially of tropicamide.

11. The method according to claim 9, wherein said composition is in a dosage form selected from the group consisting of a candy composition, a chewing gum, and a film.

12. The method according to claim 11, wherein said candy composition is selected from the group consisting of lozenges, lollipops, pastilles, troches, and chewing gums.

13. The method according to claim 11, wherein said composition is a film.

14. The method according to claim 9, wherein said excipient, when present, is selected from the group consisting of a pharmaceutically acceptable buffering agent, a plasticizing agent, a muco-adhesive agent, a stabilizing agent, a taste-masking agent, a flavoring agent, a breath freshening agent, a coloring agent, an antiseptic agent, an inert filler agent, a preserving agent, nonionic polymer, anionic polymer, softening agent, swelling agent, chelating agent, foaming agent, and combinations thereof.

15. The method according to claim 14, wherein said excipient, when present, is a muco-adhesive agent.

16. The method according to claim 1 or claim 9, wherein said active ingredient is present in said composition in an amount ranging from 0.01 to 200 milligrams, inclusive.

17. The method according to claim 16, wherein said active ingredient is present in said composition in an amount ranging from 0.01 milligrams to 50 milligrams, inclusive.

18. The method according to claim 17, wherein said active ingredient is present in said composition in an amount ranging from 0.1 milligram-20 milligrams, inclusive.

19. The method according to claim 1, wherein said individual suffers from sialorrhea or drooling.

20. The method according to claim 1 or claim 9, wherein said individual is a patient of a condition selected from the group consisting of Parkinson's Disease, Lewy body disease, cerebral palsy, amyotrophic lateral sclerosis, muscular dystrophy, multiple sclerosis, stroke, mental retardation, developmental retardation, oropharyngeal carcinoma, neuromuscular dysfunction, sensory dysfunction, motor dysfunction, parkinsonism, pseudobulbar palsy, bulbar palsy, multiple system atrophy, corticobasal degeneration, motor neuron disease, and neurodegenerative disease.

21. The method according to claim 20, wherein said condition is Parkinson's Disease.

22. The method according to claim 20, wherein said condition is cerebral palsy.

23. The method according to claim 1 or claim 9, wherein said individual is being prepared for or is undergoing a dental, orthodontic, periodontic, oral cosmetic, or oral surgical procedure.

24. The method according to claim 1 or claim 9, wherein said individual is being prepared for or undergoing electroconvulsive therapy or anesthesia used for surgery.

25. The method according to claim 1 or claim 9, wherein said individual is an animal.

26. The method of claim 1, wherein saliva production in said individual is temporarily decreased.

27. The method of claim 26, wherein saliva production in said individual is decreased for six or less hours.

28. The method of claim 26, wherein saliva production in said individual is decreased for four or less hours.

29. The method of claim 26, wherein saliva production in said individual is decreased for two or less hours.

30. The method of claim 9, wherein saliva production in said individual is temporarily decreased.

31. The method of claim 30, wherein saliva production in said individual is decreased for six or less hours.

32. The method of claim 30, wherein saliva production in said individual is decreased for four or less hours.

33. The method of claim 30, wherein saliva production in said individual is decreased for two or less hours.

* * * * *